(12) United States Patent  
Schregel

(10) Patent No.: US 6,322,513 B1  
(45) Date of Patent: Nov. 27, 2001

(54) BLOOD-VESSEL CATHETER

(76) Inventor: Werner Schregel, Heidedyk 44, D-47802 Krefeld (DE)

( * ) Notice: Subject to any disclaimer, the term of this patent is extended or adjusted under 35 U.S.C. 154(b) by 0 days.

(21) Appl. No.: 09/490,542

(22) Filed: Jan. 24, 2000

(30) Foreign Application Priority Data

Jan. 25, 1999 (DE) .............................................. 299 01 179

(51) Int. Cl.⁷ ...................................................... A61B 8/14
(52) U.S. Cl. ............................................ 600/466; 600/469
(58) Field of Search .................................... 600/447, 463, 600/467, 473, 585, 466, 454, 468, 459, 439; 606/17, 15; 604/22; 601/2

(56) References Cited

U.S. PATENT DOCUMENTS

| 4,354,502 | 10/1982 | Colley et al. . | |
|---|---|---|---|
| 5,025,778 | * 6/1991 | Silverstein et al. | 128/4 |
| 5,456,251 | 10/1995 | Fiddian-Green . | |
| 6,001,069 | * 12/1999 | Tachibana et al. | 601/2 |
| 6,059,731 | * 5/2000 | Seward et al. | 600/459 |

FOREIGN PATENT DOCUMENTS 1 510 682   5/1978   (GB) .

* cited by examiner

*Primary Examiner*—Marvin M. Lateef
*Assistant Examiner*—Ali M. Imam
(74) *Attorney, Agent, or Firm*—Herbert Dubno

(57) ABSTRACT

A catheter which can be introduced into a blood vessel as an infusion or aspirating channel opening into the blood vessel through orifices in the catheter and at least one other channel closed at the catheter end and in which an ultrasound probe is removably received. This second channel allows the probe to be withdrawn and inserted into another catheter without the necessity of sterilization.

4 Claims, 4 Drawing Sheets

BLOOD-VESSEL CATHETER

FIELD OF THE INVENTION

The invention relates to a catheter to be introduced into blood vessels and consisting of a substantially tubular instrument with at least one infusion or suction channel having at least one opening in the end area.

BACKGROUND OF THE INVENTION

By means of such catheters liquids can be injected into body cavities, e.g. blood vessels or samples can be taken from body cavities. Such catheters are also used during operations, particularly in operations where the patient is in a semi-sitting position, for the prevention and treatment of air embolisms. Air embolisms can occur when venous vessels are opened and a negative venous pressure prevails as a result of heavy blood loss, e.g. during transplants. Thereby air can be sucked into the central venous system and an accumulation of larger air volumes can occur, blocking the blood flow to the heart.

For the aspiration of such air from the central venous system, the catheter which has at least one opening, is placed in the upper vena cava at the entrance to the right atrium. When a catheter with several lateral openings is used, the point of the catheter is placed rather in the upper half of the right atrium. Through the opening or openings of the catheter, the air which may have entered the central venous system during an operation is aspirated, thereby preventing an air embolism. The disadvantage is that in order to prevent air embolisms such catheters have to be precisely placed, but their placement is not simple because the position of the catheter cannot be exactly determined from the outside.

Besides in addition to the catheter a further instrument is required, in order to detect the air which may possibly have entered the central venous system and to aspirate it by means of the catheter.

Provided that transesophagial echocardiography is used, a flexible tube with an ultrasound device at its end can be introduced into the patient's esophagus. The disadvantage of this method is that the required equipment is very expensive and that the patient has to be monitored by an additional physician not only during the operation, but also for several hours afterwards. So far this method has proven to be very costly.

In another procedure for detecting air embolisms a Doppler probe is affixed from the outside on the body of the patient in the cardiac area. The measuring results obtained this way are partially quite inaccurate since the distance between the Doppler probe affixed to the skin and the heart is large, and the resulting measuring results can be influenced by the hemostatic devices used in the operative tract, such as electrocautery. Furthermore the Doppler probe has to be very precisely placed. With patients with lung enlargement, for instance as the result of bronchitis or asthma, this procedure cannot be used at all.

OBJECT OF THE INVENTION

It is the object of the invention to indicate a catheter, particularly for the prevention and therapy of air embolisms, which avoids the aforementioned drawbacks.

SUMMARY OF THE INVENTION

This object is achieved by providing the catheter with at least one measuring device for the detection of gases in liquids. By integrating the measuring device into the catheter, the catheter can be used not only for the aspiration of air when the catheter is used for the prevention and treatment of air embolisms during operations, but also for the detection of air in liquids, such as blood. Besides the placement of the catheter is facilitated due to the integrated measuring device. Since the catheter with the measuring device is directly flushed by the liquid to be monitored, and thereby is in immediate contact with the liquid to be monitored, disturbances such as occur during conventional procedures are reduced to a minimum. Since only the measuring device or devices are integrated in the catheter, while the other components required for aspiration and injection, such as control or suction devices are arranged outside the catheter, such catheters have very small diameters.

Suitably the measuring device can be an ultrasound probe, consisting at least of one receiver and a transmitter arranged at an angle to one another. In another embodiment a measuring device radiating in several, particularly circular, directions can be provided. However it is also possible to have a combination of measuring devices offset from one another and one circularly radiating measuring device. Such probes make use of the so-called "Doppler effect", wherein the frequency change between the waves radiated from the receiver and reflected by the liquid or air bubbles, and the waves received by the receiver is established. For instance if an air bubble existing in the blood vessel flows along the ultrasound probe, the frequency of the waves reflected by the air bubble changes. This frequency change is then signalled acoustically or optically, so that the air bubble can be aspirated through the catheter openings.

In order to insure that the measuring device is reusable and does not come into direct contact with the blood when the catheter is introduced in a blood vessel, at least one insertion channel closed at its end can be provided. For this purpose the measuring device is slipped into the closed-end insertion channel, so that a contact with the liquid to be monitored is avoided. The catheter equipped this way with the measuring device is then introduced into the blood vessel.

In another embodiment of the invention, on both sides of the infusion or suction channel, closed insertion channels can be provided. Several measuring devices can be offset with respect to one another. This insures that, due to the overlapping angles of radiation, the entire vessel volume is monitored, so that air bubbles in any area of the vessel volume can be detected.

It is possible to provide the catheter with end-side and/or lateral openings for the aspiration of the detected air bubbles.

In a particularly advantageous embodiment of the invention, the measuring device or devices are arranged at a distance from the catheter end, and the catheter has lateral openings at least between the measuring devices. The catheter can be placed in such a manner that the measuring devices are located in the area entering the right atrium, so that the part of the catheter with the openings is placed in the atrium. To the extent that air bubbles are detected by the measuring devices in the blood flowing from the blood vessel via the right atrium to the heart, these air bubbles can be directly aspirated via the catheter openings following in the flow direction.

SPECIFIC DESCRIPTION

Figure 1:
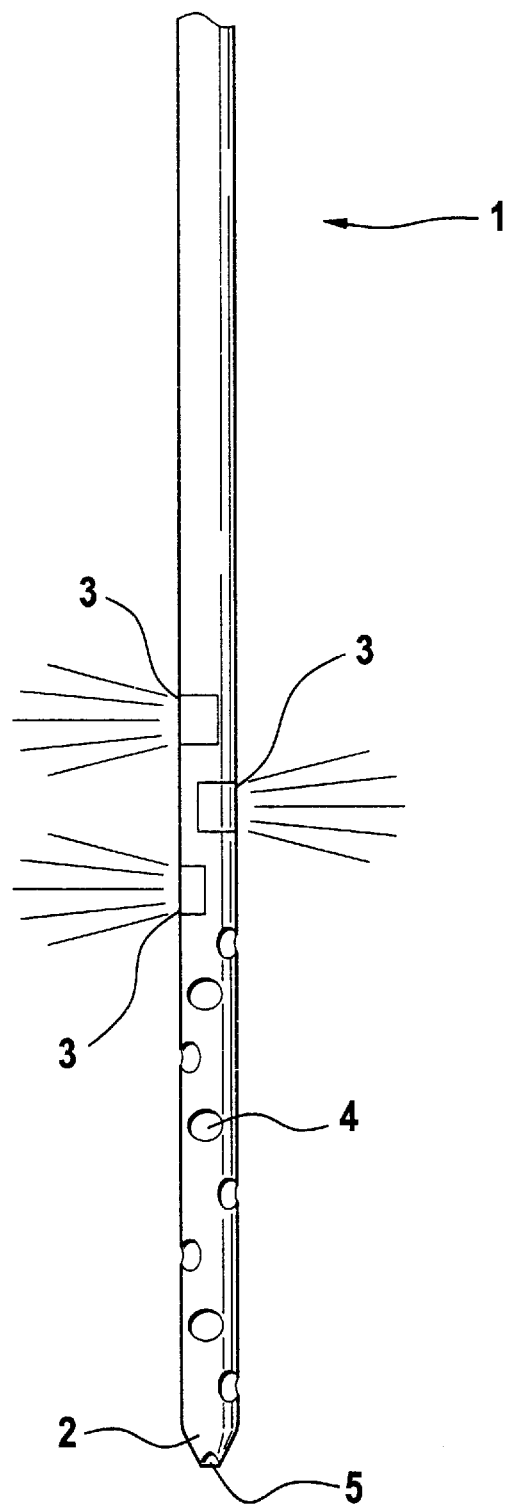
FIG. 1 is a side view of a catheter according to the invention.

In all drawing figures the same reference numerals are used for identical or similar components.

FIG. 1 shows a catheter 1 consisting of a substantially tubular instrument. The catheter 1 is introduced into a blood vessel not shown in the drawing, whereby the one end 2 with which the catheter 1 is introduced into the blood vessel is shaped like a truncated cone.

At a distance from the end 2 of catheter 1, measuring devices 3 for the detection of gases, such as air volumes in liquids are provided. The measuring devices 3 are advantageously arranged so that their radiation angles overlap, so that the entire vessel volume of the blood vessel can be monitored.

Figure 2:
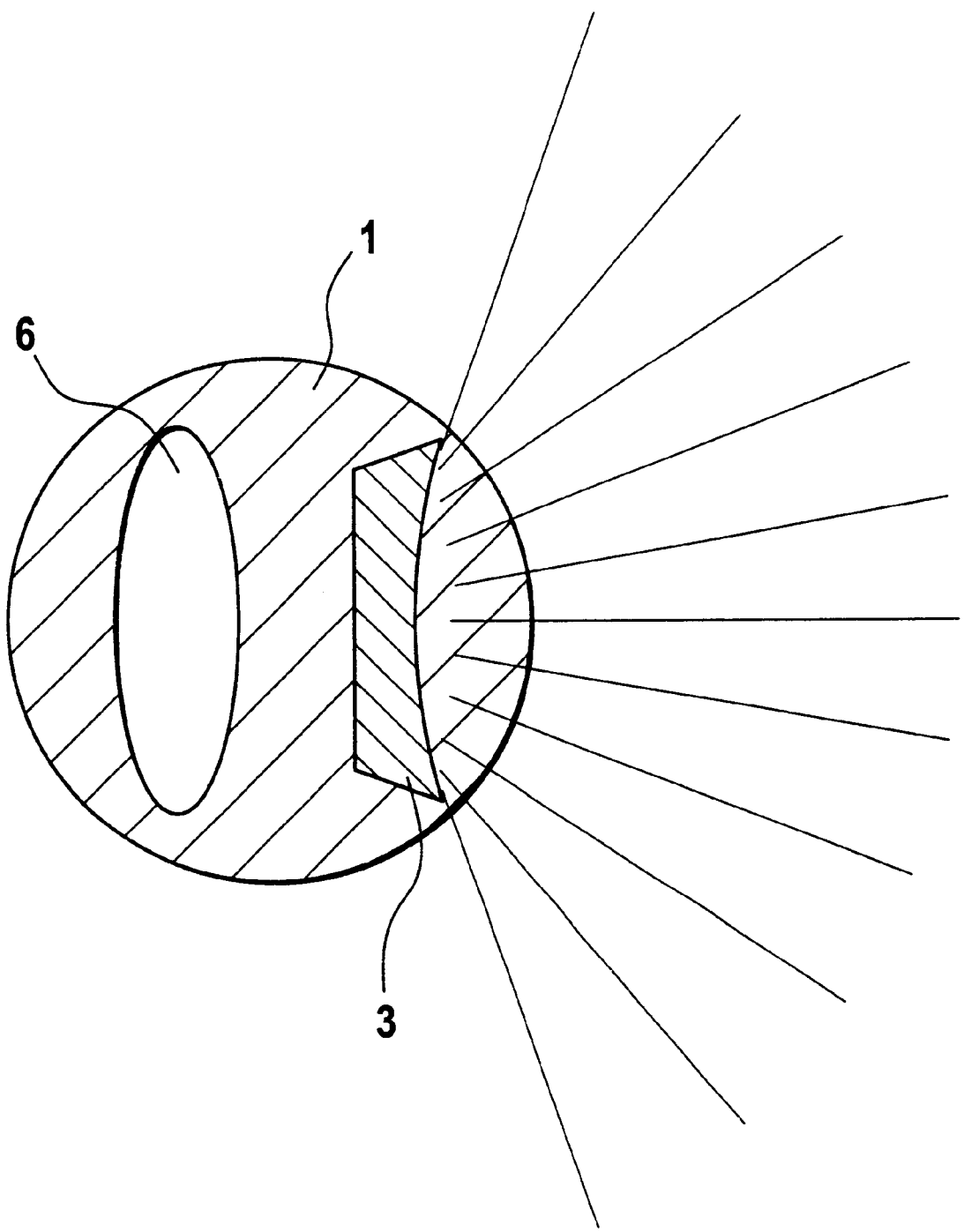
FIG. 2 is a section through a catheter with one infusion or suction channel and an integrated measuring device.

Between the measuring devices 3 and the end 2 of the catheter 1 lateral openings 4 and an end opening 5 in the area of end 2 are provided, which are connected with an infusion or suction channel 6 as shown in FIG. 2.

The other end of the catheter 1 is connected with a conventional infusion or suction device not shown in the drawing for the infusion or suction channel 6, as well as with a control and display device, also not shown in the drawing, for the measuring devices 3.

Before the surgical intervention, the catheter 1 is inserted with its end 2 in a blood vessel not shown in the drawing, and thereby placed so that the catheter 1 with the measuring devices 3 is arranged at the entrance to the right atrium since here the venous system has the largest diameter and therefore all air bubbles in the blood entering the right atrium can be better detected. The lateral openings 4 or the end-side opening 5 of the catheter are thereby located in the right atrium. If an air bubble is detected by the measuring devices 3, then the same can be aspired through the lateral openings 4 or the end opening 5 which follow the sensors 3 in the flow direction.

FIG. 2 shows a variant of the catheter 1 of the invention, wherein the measuring device 3 is firmly integrated in the catheter 1. It can be clearly seen that the measuring device 3 consists of a receiver and a transmitter, arranged at an angle to each other. The waves emitted by the transmitter are reflected by the liquid and by any air which may be present bubbles and again received by the receiver. Depending on the reflected medium, i.e. liquid or air bubbles, differences appear in the frequency of the emitted and received waves, so that by means of this technique air bubbles can be detected. Since the catheter 1 is directly flushed by the liquid, even air bubbles with minimal diameters can be measured. In this embodiment, the measuring device 3 is located in one half of the catheter 1, while the infusion or suction channel 6 is located in the other half.

Figure 3:
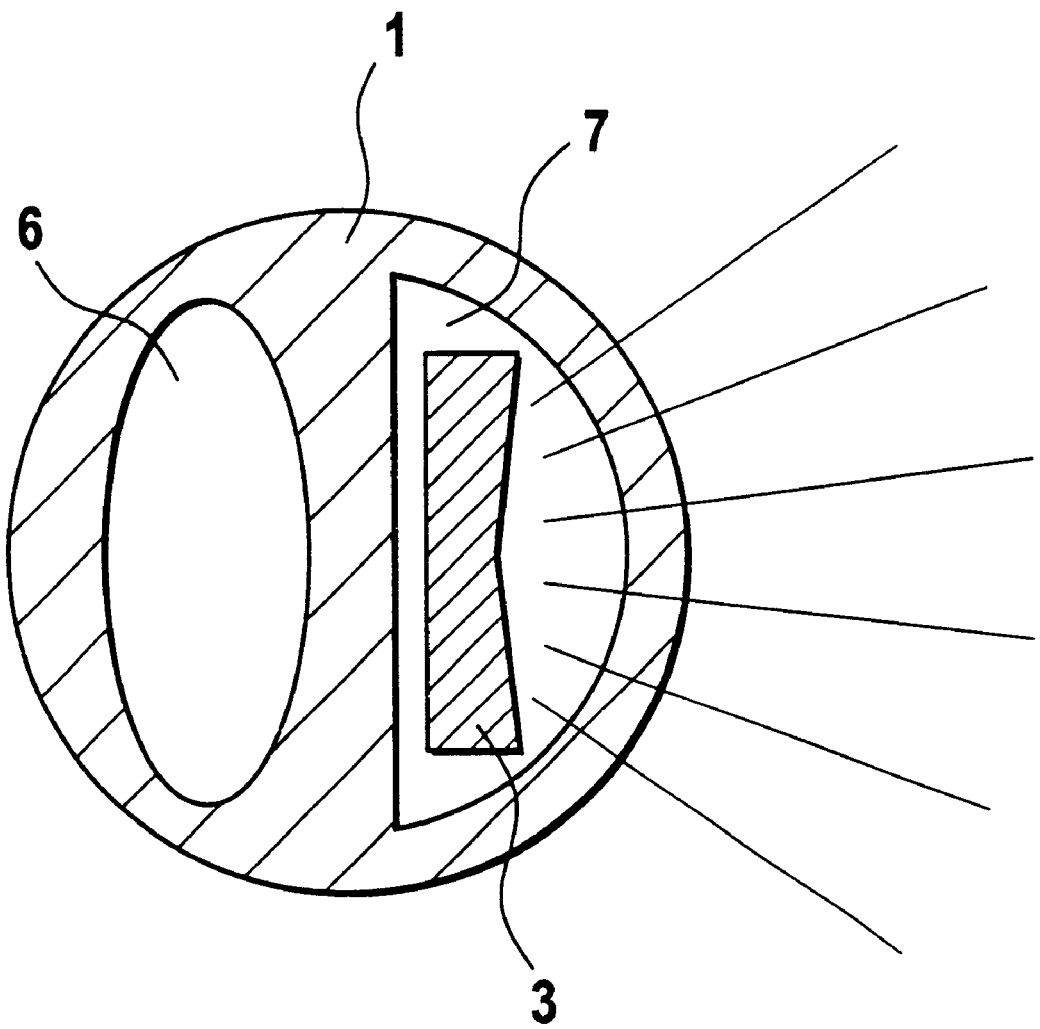
FIG. 3 is a section through a catheter with an infusion or suction channel and an insertion channel closed at an end and to which a measuring device is introduced.

FIG. 3 shows an embodiment of the catheter 1 wherein the measuring device 3 is placed in an insertion channel 7 which is closed at the end 2 and located in the catheter 1. Since the insertion channel 7 is closed at the end, the measuring device 3 which is slidable therein does not come in contact with the liquid to be monitored and flushing around the catheter 1. After the operation, the measuring device 3 can be removed from the insertion channel of the catheter 1 and introduced into a new catheter 1, thereby being reusable without needing costly sterilization. Here too the infusion or suction channel 6 is arranged in the other half of the catheter 1.

Figure 4:
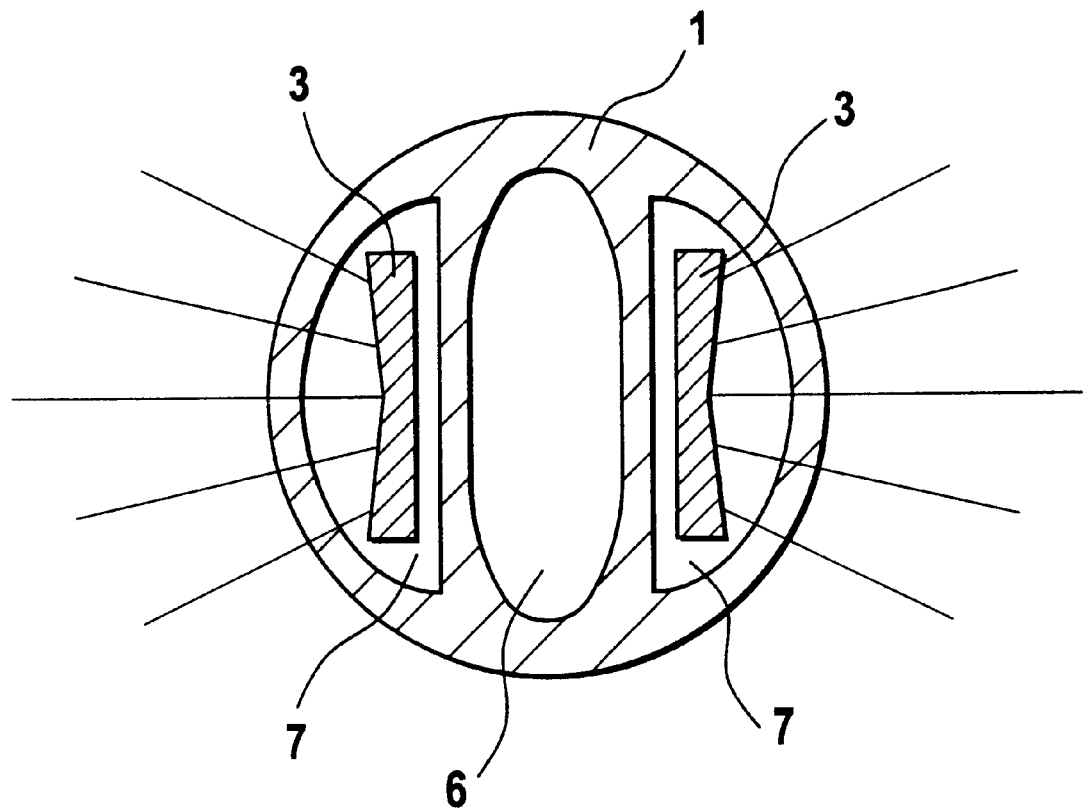
FIG. 4 is a section through a catheter with an infusion or suction channel and two insertion channels closed at the end and with a measuring device introduced in each.

In the embodiment of the catheter 1 represented in FIG. 4 the infusion or suction channel 6 is centrally arranged, whereby on both sides of the infusion or suction channel 6 insertion channels 7 closed at one end are provided. The measuring devices 3 are introduced in these insertion channels 7. In each insertion channel 7 several measuring devices 3 can be provided.

What is claimed is:

1. A catheter adapted to be introduced into a blood vessel and for detection and removal of air emboli in said blood vessel, said catheter comprising an elongated tubular instrument having a generally conical end and formed with a first channel selectively connectable to an infusion and suction device, a plurality of openings along said instrument connected to said first channel for selectively infusing a substance into said vessel and for aspirating air therefrom, and a second channel extending along said instrument separated from said first channel and closed at said end; and at least one ultrasound probe for detecting a quantity of air in said vessel, said probe being received in said second channel and being removable by longitudinally withdrawing said probe from said second channel.

2. The catheter defined in claim 1 wherein said ultrasound probe comprises at least one receiver and at least one transmitter disposed at an angle to one another.

3. The catheter defined in claim 2 wherein a respective one of said openings is provided at said end of said instrument.

4. The catheter defined in claim 3 wherein said instrument has a third channel extending along said instrument and separated from said first and second channels, said third channel being closed at said end and receiving at least one further ultrasound probe removable from said third channel for detecting said quantity of air in said vessel.

* * * * *